Figure 1:
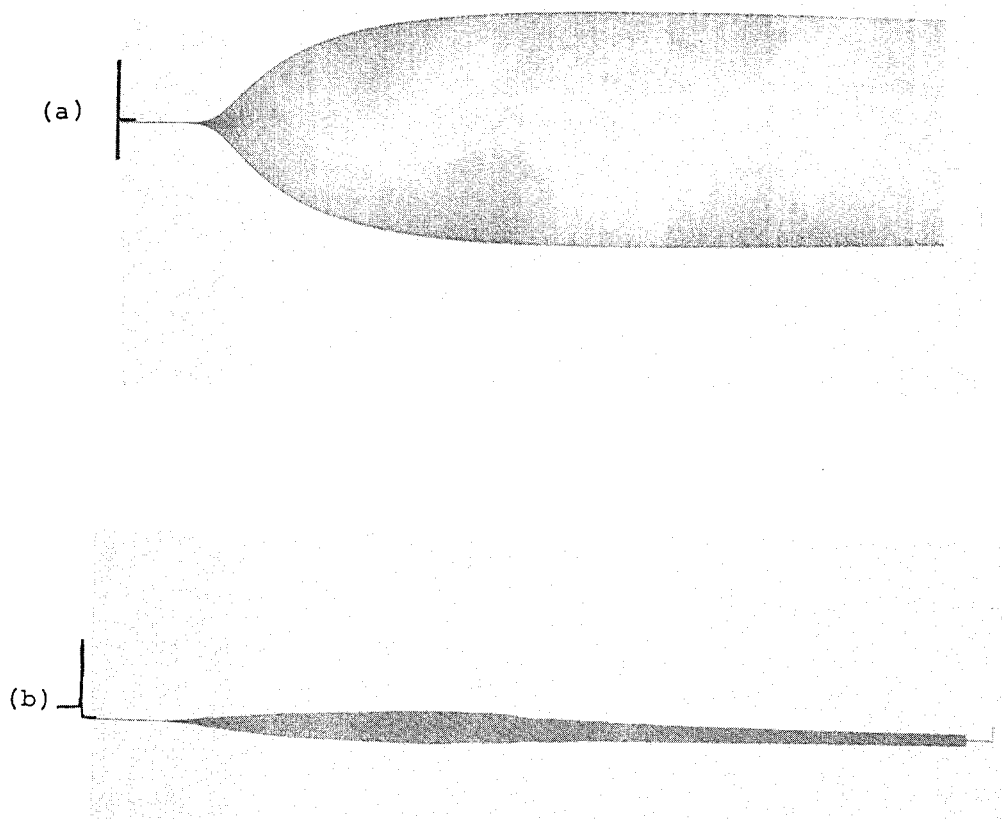

United States Patent [19]

Durrani

[11] Patent Number: 4,792,599
[45] Date of Patent: Dec. 20, 1988

[54] BIOCOMPATIBLE POLYESTERS
[75] Inventor: Aziz A. Durrani, London, England
[73] Assignee: Biocompatibles Ltd., London, England
[21] Appl. No.: 162,337
[22] PCT Filed: Jul. 28, 1987
[86] PCT No.: PCT/GB87/00533
    § 371 Date: Mar. 3, 1988
    § 102(e) Date: Mar. 3, 1988
[87] PCT Pub. No.: WO88/00956
    PCT Pub. Date: Feb. 11, 1988
[30] Foreign Application Priority Data
    Jan. 28, 1986 [GB] United Kingdom ............. 8618334
[51] Int. Cl.$^4$ ............... C08G 63/66; A61L 27/00; A61L 31/00
[52] U.S. Cl. ............... 528/272; 528/287; 528/288; 528/299; 528/398; 528/399; 528/400; 528/425; 528/950; 523/105; 523/112; 523/113; 523/200; 523/205; 623/1; 623/11; 623/13; 424/78
[58] Field of Search ............. 528/272, 287, 288, 299, 528/398, 399, 400, 425, 950; 424/31, 23, 33; 523/105, 112, 113, 200, 205

[56] References Cited
U.S. PATENT DOCUMENTS
4,689,386 8/1987 Chapman et al. ............. 528/71

FOREIGN PATENT DOCUMENTS
0326922 1/1976 Austria .
0057116 8/1982 European Pat. Off. .
8602933 5/1986 PCT Int'l Appl. .

Primary Examiner—John Kight
Assistant Examiner—S. A. Acquah
Attorney, Agent, or Firm—Nixon & Vanderhye

[57] ABSTRACT

A biocompatible polyester comprising repeating units derived from glycerophosphorylcholine or glycerophosphorylethanolamine and at least one di- or polyfunctional acid or reactive derivative thereof is haemocompatible and may be used in components for handling body fluids and in prostheses.

19 Claims, 1 Drawing Sheet

BIOCOMPATIBLE POLYESTERS

The present invention relates to polyester materials having biocompatible properties, in particular polyesters involving repeating units derived from glycerophosphorylcholine.

Blood contacting devices are of major importance in the practice of modern medicine but suffer from the problem that, when a foreign surface is brought into contact with blood, absorption of certain blood components results in the formation of blood clots. Previous solutions to this problem included coating any surfaces of the devices which will come into contact with blood with haemocompatible materials, for instance materials mimicking the inert surfaces of, red or white blood cells. Experiments with phosphatidylcholine polymers indicate that these substances do not alter (reduce) the blood clotting time.

There are certain disadvantages involved in coating these devices and further investigation has enabled identification of materials which have biocompatible surfaces without the need for a coating treatment.

Accordingly, the present invention provides a biocompatible polyester comprising repeating units derived from glycerophosphorylcholine (GPC) or glycerophosphorylethanolamine (GPE) and at least one di- or poly-functional acid or reactive derivative thereof.

Polyesters according to the present invention are derived from the compounds of formula (I)

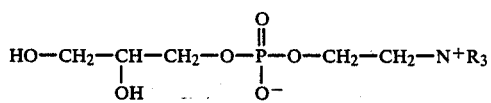

wherein R is hydrogen (GPE) or methyl (GPC).

GPC is a bifunctional alcohol which may be isolated from egg or soyabean lecithins in the form of its cadmium chloride complex. This dihydric alcohol may be treated with a bifunctional acid or active derivative thereof such as an acid chloride to make a linear polyester. For branched chain polyesters a polyfunctional, e.g., a trifunctional, acid or reactive derivative such as an acid chloride may be used.

The linear polyesters of GPC or GPE according to the present invention comprise repeating units of formula (II)

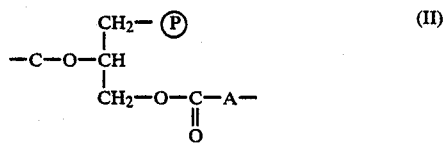

wherein —A— is straight or branched $C_{1-15}$ alkylene or straight or branched $C_{2-15}$ alkenylene and ⓟ is a phosphate head group of formula (III)

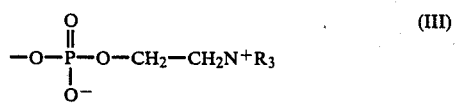

wherein R is methyl or hydrogen.

Branched chain polyesters will have corresponding repeating units but having branch points in the residues of the polyfunctional acids.

The physical properties of the polyester may be adjusted by incorporation of various other monomers, examples of which are as follows: The softness of the polyesters is controlled by including other dihydric alcohols in the reaction mixtures. Incorporation of some long chain diols along with GPC or GPE produces polymers with more elasticity. Ethylene glycol may be added to produce polymers having lower melting points than those containing GPC or GPE as sole diol.

Branched chain polyesters are more insoluble than the linear materials and also have greater solidity. High amounts of GPC or GPE in these esters increases their melting points. Some high GPC or GPE branched chain polymers decompose on heating.

Preferred polyesters according to the present invention include repeating units derived from one of more of the following-
  (1) Acid Chlorides
Isophthaloyl chloride and phthaloylchloride
Benzene 1,3,5-triacid chloride
Benzene 1,2,4-triacid chloride
Adipoyl chloride
Fumaryl chloride
Malonyl chloride
  (2) Acids
Isophthalic and phthalic acids
Benzene 1,3,5- and 1,2,4-tricarboxylic acids
Adipic Acid
Fumaric Acid
Malonic Acid
  (3) Alcohols
Ethylene glycol
1,2-Propanediol
1,2- and 1,4-Butane diols
2,5- and 1,6-Hexane diols
1,7-Heptanediol
1,8-Octane diol
Glycerol In a particular preferred aspect the polyesters according to the invention comprise units derived from GPC and GPE. More preferably such repeating units are present in a molar ratio of 99:1 to 50:50, most preferably 80:20, GPC derived units to GPE derived units.

The present invention also includes a physical admixture of GPC polyester and GPE polyester as descrbed above, preferably in proportions affording molar ratios of GPC- and GPE- derived repeating units as mentioned above.

Polyesters according to the invention are advantageous in being haemocompatible at any exposed surface. This allows articles formed of the polyesters to be shaped, and worked after crude shaping, without, subsequent coating treatment. Moreover, scratching or other damage to the surfaces of such articles simply exposes fresh haeomocompatible material. Polyesters according to the present invention may be used to prepare artificial tendons, blood vessels, fibres for aorta, fibres for autogenised and lyophilised for blood, vascular grafts and polyester polypropylene for cranioplasty. These polyesters may also have applications to tissue culture systems where particular cell adhesion characteristics are required.

The present invention also provides a process for producing GPC or GPE polymers as defined above which comprises reacting GPC or GPE with at least one di- or poly-functional acid or reactive derivative thereof.

GPC or GPE may be the sole alcohol present in the reaction mixture or there may be other diols and/or polyols. Preferably GPC, GPE or an appropriate mixture thereof represents at least 50 mole% of the di- or poly-ols in the reaction mixture, more preferably at least 75% and most preferably 90% or more. Suitable acids include di- and poly-carboxylic acids, preferably di- or trialkanoic acids. Suitable reactive derivatives of acids include the acid halides, especially acid chlorides. Conveniently at least 50 mole% of the total amount of di- or poly-acids or reactive derivatives thereof is provided by one or a mixture of di-alkanoic acids, which are preferably straight chain di-alkanoic acids having from 3 to 12 carbon atoms, or reactive derivatives thereof. For the formation of a high molecular weight polyester it is important that accurate amounts of the reactants are used since an excess of either reactant will cause premature chain termination. Ideally the reaction mixture comprises substantially equal numbers of alcohol groups and acid groups or reactive derivatives thereof.

Preferably the esterification is conducted in the presence of an inert solvent, preferably an ether solvent. When the esterification is conducted using acid halides, suitably an organic base such as pyridine is present, whereas when the reaction involves free acids it is suitably conducted in an apparatus designed for azeotropic removal of water and in the presence of an acid, such as concentrated sulphuric acid, as catalyst.

Polyesters according to the present invention may be shaped or formed in conventional manner to provide tubing, components, prostheses and other devices having haemocompatible surfaces.

Accordingly the present invention also provides a shaped article comprising a polyester of GPC or GPE as hereinbefore described.

The invention will be illustrated by the following non-limiting Examples and with reference to the accompanying drawings in which:

FIG. 1. Shows thromboelastographs generated using (a) an uncoated pin and cuvette and (b) a pin and cuvette coated with polyester according to the present invention.

EXAMPLE 1

Isophthaloyl chloride (20.3 g) was dissolved in anhydrous tetrahydrofuran (50 ml) and was added dropwise in a thoroughly stirred, cooled (0° C.) mixture of ethylene glycol (3.1 g), GPC CdCl$_2$ (12.85 g) and pyridine (25 ml) in anhydrous tetrahydrofuran (75 ml). The addition took place over 30 minutes after which the stirring was continued for another 6 hours at room temperature. The mixture was concentrated (40°-50° C.; 1.5 mm Hg) to about one third of the original volume and diluted with water (500 ml) and mixed well. Water was decanted and the residue was washed with fresh portions of water (50 ml) and the white polyester filtered on a Buchner funnel. On drying, the material weighed 15 g.

The above process was repeated using diethyl ether instead of tetrahydrofuran.

EXAMPLE 2

Adipoyl chloride (1.83 g), dissolved in anhydrous diethyl ether (10 ml) was added dropwise over 15 minutes to a cooled (0° C.) and rapidly stirred mixture of GPC CdCl$_2$ (4.58 g) dried pyridine (5 ml) in diethyl ether (25 ml). The mixture was then stirred at room temperature for 6 hours after which the ether was evaporated and the residue washed with water (4×25 ml). The white polyester was finally sucked dry to obtain 5.89 g of the dried material.

The above process was repeated using tetrahydrofuran as a solvent instead of the ether.

EXAMPLE 3

GPC CdCl$_2$ (25.7 g) was suspended in 50 ml of tetrahydrofuran (or diethyl ether), pyridine (25 ml) added and treated with isophthaloyl chloride (20.3 g) in 50 ml tetrahydrofuran (or diethyl ether) as described in Examples 1 and 2. The polyester was obtained by precipitation with water, washed and sucked dry. Yield 14.9 g.

EXAMPLE 4

GPC CdCl$_2$ (12.85 g) and ethylene glycol (3.1 g) was suspended in 50 ml of tetrahydrofuran (or diethyl ether), pyridine (25 ml) added and treated with benzene-1,2,4-triacid chloride in tetrahydrofuran (or diethyl ether) (50 ml) as described in Examples 1 and 2 to produce a CPC polyester.

EXAMPLE 5

GPC CdCl$_2$ (25.7 g) was suspended in 50 ml of tetrahydrofuran (or diethyl ether), pyridine (25 ml) add and treated with benzene-1,2,4-triacid chloride in tetrahydrofuran (or diethyl ether) (50 ml) as described in Examples 1 and 2 to produce a GPC polyester.

EXAMPLE 6

GPC CdCl$_2$ (9.16 g) and isophthalic acid (3.32 g) were mixed in toluene (150 ml) and conc. sulphuric acid (0.5 ml) added. The mixture was heated at reflux under Dean and Stark apparatus for the removal of the water thus formed. The reflux was continued till no more water could be removed (12 hours). Solvent was removed (80° C.; 15 mm Hg) and the residue was suspended in water (100 ml) in which sodium carbonate (20 g) was dissolved. The white solid was filtered under suction and washed repeatedly with water. The yield of the dried white solid was 8.3 g.

EXAMPLE 7

GPC polyesters were produced in similar manner to Examples 1 to 6 using fumaryl chloride or malonyl dichloride as acid chlorides.

EXAMPLE 8

GPE polyesters are produced in similar manner to the GPC polyesters of Examples 1 to 7.

The polyesters prepared in Examples 1 to 6 were all soluble in DMSO and were characterised by the presence of choline residues, aromatic nuclei (if present) and ester bond protons, by $^1$H-NMR. The IR spectra also show the presence of ester bonds.

EXAMPLE 9

The biocompatibility, particularly the haemo compatibility of polyesters prepared according to the present invention may be assessed using a thromboelastograph. The thromboelastograph is a mechanical optical system which provides a continual visual and photokymographic observation of blood during all phases of coagulation. Using this equipment it is possible to measure (r) the coagulation time, (k) the rapidity of the fibrin build up, and E the elastic modulus of the clot. To carry out the test, blood is placed in a plastic cuvette connected to a moving device which enables it to be oscillated back and forth over an angle of 4° 45' (1/12 radian) around a vertical axis. A pin made of steel is lowered by means of a torsion wire into the cuvette leaving a space of 1 mm for the blood sample between the pin and the cuvette. A mirror attached to the torsion wire reflects light from a slit lamp onto a strip of photographic film. Whilst the sample remains fluid the metal pin remains motionless. As fibrin formation proceeds between the cuvette and the pin, the pin is caused to oscillate proportionately.

This type of experiment gives rise to thromboelastograms. A comparison shown in FIG. 1 illustrates the marked difference which occurs in blood clot behaviour when an uncoated pin and cuvette are used (a) and the result (b) of coating a metal pin and cuvette with poly(glycerophosphorylcholine ethylene glycol orthophthalate), a polyester synthesized in the manner indicated above. It can be seen that the coagulation and fibrin formation are extremely reduced, consistent with the properties of a haemocompatible or biocompatible material.

PREPARATIVE EXAMPLE A

Synthesis of racemic phosphatidylcholine 1,2-Isopropylidine glycerol (ex Aldrich) (6.6 g) was added dropwise to a cooled (0° C.) mixture of choline acetate dichlorophosphate (20 g) (EP-A-0157469) nitromethane (100 ml) and dried pyridine (20 ml) with rapid stirring. The addition took place 15 mintues and the mixture was stirred for an additional 30 minutes. It was then treated with small portions of sodium bicarbonate till no more effervescence was noticed. The solid was removed and discarded while the filtrate was concentrated to dryness and then kept at 0.01 mm Hg over $P_2O_5$ for 48 hours. The $^1$H-NMR spectrum of rthis substance as well as that of its cadmium chloride complex are identical to that obtained from egg lecithin and its cadmium chloride complex respectively except that the unpurified synthetic product showed more protons for the choline residue due to the excess of choline acetate dichlorophosphate used in synthesis.

PREPARATIVE EXAMPLE B

Synthesis of racemic phosphatidylethanolamine 2-chloro-2-oxo-1,2,3-oxazapholane (EP-A-0157469) (14.15 g) was treated with anhydrous pyridine (5 ml) at 0° C. and anhydrous nitromethane (50 ml) added. The mixture was vigourously stirred and was treated with dropwise addition of 1,2-isopropylidine glycerol (ex Aldrich) (13.2 g) at 0° C. The addition took 15 minutes and the mixture was stirred for an additional 30 minutes. The product was then treated with crushed ice (50 g) followed by treatment with 10% hydrochloric acid (100 ml). The volatile matter was evaporated (60° C.; 15 mm Hg) and the residue was washed twice with chloroform. The substance was dried in a desiccator over $P_2O_5$ at 0.01 mm Hg for 48 hours. $^1$H-NMR of this product agreed with its structure.

I claim:

1. A biocompatible polyester comprising repeating units derived from glycerophosphorylcholine or glycerophosphorylethanolamine and at least one di- or poly-functional acid or reactive derivative thereof.

2. A polyester according to claim 1 comprising repeating units of formula (II)

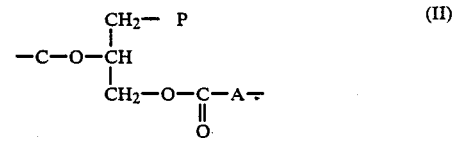

wherein —A— is straight or branched $C_{1-15}$ alkylene or straight or branched $C_{2-15}$ alkenylene and P is a phosphate head group of formula (III)

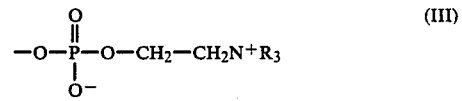

wherein R is methyl or hydrogen.

3. A polyester according to claim 1 comprising repeating units derived from 1 or more of isophthaloyl chloride, phthaloyl chloride, benzene 1,3,5-triacid chloride, benzene 1,2,4-tricarboxylic acid chloride, adipoyl chloride, fumaryl chloride, malonyl chloride, isophthalic acid, phthalic acid, benzene 1,3,5-tricarboxylic acid, benzene 1,2,4-tricarboxylic acid, adipic acid, fumaric acid and malonic acid.

4. A polyester according to claim 1 further comprising repeating units derived from a di-hydric alcohol.

5. A polyester according to claim 4 further comprising repeating units derived from ethylene glycol, 1,2-propanediol, 1,2-butane diol, 1,4-butane diol, 2,5-hexane diol, 1,6-hexane diol, 1,7-heptanediol, 1,8-Octane diol or glycerol.

6. A polyester according to claim 5 wherein the dihydric alcohol is ethylene glycol.

7. A polyester according to claim 4 wherein the dihydric alcohol is a long chain diol.

8. A polyester according to claim 1 comprising repeating units derived from glycerophosphorylcholine and repeating units derived from glycerophosphorylethanolamine.

9. A polyester according to claim 8, comprising repeating units derived from glycerophosphorylcholine and glycerophosphorylethanolamine in a molar ratio of from 99:1 to 50:50.

10. A polyester according to claim 8, comprising repeating units derived from glycerophosphorylcholine and glycerophosphorylethanolamine in a molar ratio of about 80:20.

11. A polyester material comprising a physical admixture of a polyester according to claim 1 having repeating units derived from glycerophosphoryl choline and a polyester according to claim 1 having repeating units derived from glycerophosphoryl ethanolamine.

12. A process for producing a polyester according to claim 1 comprising reacting glycerophosphorylcholine or glycerophosphorylethanolamine with at least one di- or poly-functional acid or reactive derivative thereof.

13. A process according to claim 12 comprising reacting glycerophosphorylcholine or glycerophosphorylethanolamine with a di- or poly-carboxylic acid or an acid halide of a di- or poly-carboxylic acid.

14. A process according to claim 13 comprising reacting glycerophosphorylcholine or glycerophosphorylethanolamine with a di- or tri-alkanoic acid or the acid halide of a di- or tri-alkanoic acid.

15. A process according to claim 13 wherein the acid halide is an acid chloride.

16. A haemocompatible article having a polyester according to claim 1 on at least a part of the surface thereof.

17. A haemocompatible article formed of a polyester according to claim 1.

18. A haemocompatible article having a polyester according to claim 11 on at least part of the surface thereof.

19. A haemocompatible article formed of a polyester according to claim 11.

* * * * *